(12) United States Patent
Holmqvist (10) Patent No.: US 9,861,754 B2
(45) Date of Patent: Jan. 9, 2018

(54) MEDICAMENT DELIVERY DEVICE

(71) Applicant: Carebay Europe Ltd, Swatar (MT)

(72) Inventor: Anders Holmqvist, Värmdö (SE)

(73) Assignee: Carebay European Ltd, Sliema (MT)

( * ) Notice: Subject to any disclaimer, the term of this patent is extended or adjusted under 35 U.S.C. 154(b) by 572 days.

(21) Appl. No.: 14/412,624

(22) PCT Filed: Jun. 12, 2013

(86) PCT No.: PCT/EP2013/062083
§ 371 (c)(1),
(2) Date: Jan. 2, 2015

(87) PCT Pub. No.: WO2014/005808
PCT Pub. Date: Jan. 9, 2014

(65) Prior Publication Data
US 2015/0151053 A1 Jun. 4, 2015

Related U.S. Application Data

(60) Provisional application No. 61/669,024, filed on Jul. 7, 2012.

(30) Foreign Application Priority Data

Jul. 6, 2012 (SE) ...................................... 1250790

(51) Int. Cl.
*A61M 5/315* (2006.01)
*A61M 5/24* (2006.01)
*A61M 5/31* (2006.01)

(52) U.S. Cl.
CPC .......... *A61M 5/31541* (2013.01); *A61M 5/24* (2013.01); *A61M 5/31525* (2013.01);
(Continued)

(58) Field of Classification Search
CPC .......... A61M 5/31541; A61M 5/31551; A61M 5/31585; A61M 5/31535; A61M 5/31525; A61M 5/24; A61M 2005/3154
See application file for complete search history.

(56) References Cited

U.S. PATENT DOCUMENTS 5,925,021 A   7/1999   Castellano et al.
7,094,221 B2 *  8/2006   Veasey .............. A61M 5/31551
                                                                    604/187

(Continued)

FOREIGN PATENT DOCUMENTS

EP          0554996 A1   8/1993
WO    2004/002556 A1   1/2004
(Continued)

OTHER PUBLICATIONS

EPO, Int'l Search Report in PCT/EP2013/062083, dated Oct. 10, 2013.
EPO, Written Opinion in PCT/EP2013/062083, dated Oct. 10, 2013.

*Primary Examiner* — Andrew Gilbert
(74) *Attorney, Agent, or Firm* — Piedmont Intellectual Property (57) ABSTRACT

The present invention relates to a medicament delivery device (100) having a a drive mechanism arranged to drive a plunger rod (12). A last dose limiting mechanism is arranged to interact with the drive mechanism and limit the distal end position of an actuator (3) when the plunger rod (12) has reached a pre-determined position between its distal end position and its proximal end position.

19 Claims, 6 Drawing Sheets

(52) U.S. Cl.
CPC .... *A61M 5/31551* (2013.01); *A61M 5/31585* (2013.01); *A61M 5/31543* (2013.01); *A61M 2005/2407* (2013.01); *A61M 2005/3126* (2013.01)

(56) References Cited

U.S. PATENT DOCUMENTS

| | | | |
|---|---|---|---|
| RE41,956 E | * | 11/2010 | Klitgaard ........... A61M 5/31511 604/181 |
| 2006/0153693 A1 | | 7/2006 | Fiechter et al. |
| 2007/0016142 A1 | * | 1/2007 | Burren .................... A61M 5/24 604/207 |
| 2008/0154211 A1 | * | 6/2008 | Moller .............. A61M 5/31536 604/211 |
| 2009/0254044 A1 | * | 10/2009 | Kohlbrenner ........... A61M 5/20 604/207 |
| 2009/0299297 A1 | * | 12/2009 | Moller .................... A61M 5/24 604/211 |
| 2010/0324494 A1 | * | 12/2010 | Plumptre .......... A61M 5/31551 604/207 |
| 2011/0004191 A1 | * | 1/2011 | Jones ................ A61M 5/31538 604/506 |
| 2012/0029443 A1 | * | 2/2012 | Holmqvist .............. A61M 5/20 604/211 |

FOREIGN PATENT DOCUMENTS

| | | |
|---|---|---|
| WO | 2007/017052 A1 | 2/2007 |
| WO | 2009/092807 A1 | 7/2009 |
| WO | 2010/115670 A1 | 10/2010 |
| WO | 2010/139643 A1 | 12/2010 |
| WO | 2011/089246 A1 | 7/2011 |
| WO | 2014/005807 A1 | 1/2014 |

* cited by examiner

MEDICAMENT DELIVERY DEVICE

FIELD OF THE INVENTION

The present invention relates to a medicament delivery device, especially a multidose reusable injection device comprising a last dose limiting mechanism that prevents a user from setting a dose that exceeds the remaining contents of the container.

BACKGROUND OF THE INVENTION

Reusable injectors which can be reloaded with a new medicament container when a prior medicament container is emptied are known from prior art. For example, pen injectors for insulin are commonly known.

WO-2004/002556 discloses a re-usable pen injector for use with containers. The device comprises a dose setting mechanism for setting a required dose to be injected and a drive mechanism having a plunger rod acting on a plunger in the container. When the container has been emptied to a pre-defined extent, the plunger rod can be reset to an initial position by unscrewing the two housing parts. If a user of such prior art injectors sets a dose that is larger than the remaining amount of medicament in the container this will only become apparent to the user when the container is completely emptied, i.e. the plunger rod comes to a stop. This brings about at least two problems, the first being that the user has to reload the device with a new container and immediately perform another injection which can be perceived as inconvenient and tiresome. The second being the fact that even if the user is prepared to perform such subsequent injection, the user often does not know how much medicament was injected in the first injection and thus does not know how much has to be injected in the second injection which can endanger patient safety.

U.S. Pat. No. 5,925,021 describes an injection device which has a microprocessor coupled to it. This microprocessor has among other things the function that it prevents a user from setting a larger dose than the amount of medication left in the container. A major drawback is that it relies on batteries to function, which also impairs reliability of service.

SUMMARY OF THE INVENTION

It is an object of the invention to provide a medicament delivery device with improved user friendliness. In particular, it is an object of the present invention to provide a multidose reusable injection device that prevents a user from setting a higher dose than what is left in the container. This object and other objects are solved by an injection device as defined in claim 1. Preferred embodiments of the present invention are defined in the dependent claims.

Thus, in accordance with an aspect of the present invention, there is provided a medicament delivery device having a proximal end and a distal end, the medicament delivery device comprising a front housing and a rear housing which are interconnected and axially displaceable relative to each other between an extended position and a retracted position. A plunger rod is moveable between a proximal end position and a distal end position and is arranged to act on a plunger of a medicament container such that e.g. a medicament can be expelled by the device and a drive mechanism is arranged to drive the plunger rod. An actuator is connected to the front and rear housings respectively and axially moveable in the front and rear housings between a proximal end position and a distal end position and the actuator is biased by a first biasing member towards its distal end position. A drive sleeve is releasably connected to the actuator and arranged to act on the drive mechanism in order to drive the plunger rod. A locking ring is rotatably arranged at a distal end of the rear housing and is in threaded connection with an outer surface of the actuator and is prevented from axial movement relative to the rear housing. A release button is arranged on the rear housing which is moveable between an active and an inactive state. In the active state, the release button allows unidirectional rotational movement of the locking ring relative to the rear housing such that the actuator can move axially towards its proximal end position under rotational movement of the locking ring and when the release button is in its inactive state it allows bidirectional rotational movement of the locking ring relative to the rear housing such that the actuator can move axially towards its proximal end position or towards its distal end position under rotational movement of the locking ring. The proximal end position of the actuator is defined by the axial position of the rear housing such that by adjusting the relative axial position of the front housing and the rear housing the length of stroke between the distal end position of the actuator and the proximal end position of the actuator is determined, thereby enabling setting of a required medicament dose. A last dose limiting mechanism is arranged to interact with the drive mechanism and limit the distal end position of the actuator when the plunger rod has reached a pre-determined position between its distal end position and its proximal end position.

The construction with a last dose limiting mechanism has the advantage that the user cannot set a higher dose than that remaining in the container. Thereby the user has the choice of injecting the required dose in two steps using the present container first and then load a new cartridge or to discard the present container immediately and change to a new container so that the required dose can be injected in one single step.

In accordance with an embodiment of the medicament delivery device according to the invention, the drive mechanism comprises a drive nut fixedly arranged near a proximal end of the front housing. The nut comprises a through-bore, a part of which is provided with an inner thread. A hollow drive rod having an outer thread is unidirectionally rotatably mounted with a proximal end thereof in the drive nut and the drive sleeve is arranged in threaded connection with the outer thread of the hollow drive rod. The plunger rod, in turn, is arranged within the hollow drive rod and is in threaded connection with the inner thread of the bore of the drive nut. The plunger rod and the hollow drive rod are arranged to mate with each other such that axial movement of the plunger rod relative to the hollow drive rod is allowed while rotation of the plunger rod relative to the hollow drive rod is prevented. This arrangement will convert the linear movement of the drive sleeve into a rotational movement of the hollow drive rod and the plunger rod which will then also rotate due to the fact that it is prevented from rotation relative to the hollow drive rod. The plunger rod, being in threaded connection with the inner thread of the bore of the drive nut will be driven axially forward towards a proximal end of the medicament delivery device when the plunger rod rotates, thus forcing the plunger of a medicament container held in the medicament delivery device forwardly.

In accordance with an embodiment of the medicament delivery device according to the invention, the last dose limiting mechanism comprises a last dose sleeve which is rotatably arranged within the actuator and enclosing at least partly the hollow drive rod and is provided with an external thread. A stop ring is arranged in threaded connection with the external thread of the last dose sleeve and it is arranged to mate with the actuator such that rotation of the stop ring relative to the actuator is prevented.

This has the result that a rotational movement of the last dose sleeve results in an axial movement of the stop ring from a distal end position towards a proximal end position along the length of the last dose sleeve. The actuator comprises an abutment surface arranged to interact with the stop ring. When the stop ring moves axially along the length of the last dose sleeve it will move towards the abutment surface of the actuator. This means that when a user brings the release button towards its inactive state, releasing the locking ring such that the actuator moves towards its distal end position the distal end position has been shifted towards the proximal end position of the medicament delivery device, thus effectively reducing the length of stroke of the actuator which in turn reduces the maximum dose to be set.

In accordance with an embodiment of the medicament delivery device according to the invention, the plunger rod is provided with a funnel-like widening surface near a distal end thereof and the hollow drive rod is provided with a radially displaceable clutch which can be brought into contact with the last dose sleeve by the a funnel-like widening surface of the plunger rod. Thereby, rotation of the hollow drive rod, and thus the plunger rod, will cause the last dose sleeve to rotate causing axial displacement of the stop ring towards the proximal end of the device thereby re-locating the distal end position of the actuator towards the proximal end of the device thereby preventing the setting of a medicament dose that exceeds an amount of medicament remaining in the medicament container.

In accordance with an embodiment of the medicament delivery device according to the invention, the drive sleeve is arranged within and axially moveable relative to the actuator and coupling means are arranged to prevent the drive sleeve and the actuator from rotational movement relative to each other when the drive sleeve is in a distal axial end position relative to the actuator.

This is a simple and reliable solution to the fact that the drive sleeve will have to rotate relative to the unidirectionally rotatable hollow drive rod during release, i.e. when the release button is in its inactive state and the actuator and the drive sleeve assume their distal end positions, while the actuator itself may be perform this movement linearly.

In accordance with an embodiment of the medicament delivery device according to the invention, the coupling means comprises a tooth coupling provided on an inside surface of a distal end of the actuator. Other solutions are obviously imaginable, such as providing the surfaces with sand paper-like properties or other friction enhancing means.

In accordance with an embodiment of the medicament delivery device according to the invention, a pitch of the tooth coupling is the same or less than a pitch of the threaded connection between the drive sleeve and the hollow drive rod. This ensures that the tooth coupling between the drive sleeve and the actuator will not connect "one tooth too early" which would reduce the contact surface between the drive sleeve and the actuator unnecessarily. Using a pitch of the tooth coupling which is larger than the pitch of the threaded connection between the drive sleeve and the hollow drive rod will not bring any advantages since the maximal linear contact surface between the teeth will be defined by the pitch of the treaded connection between the drive sleeve and the hollow drive rod anyway.

In accordance with an embodiment of the medicament delivery device according to the invention, a second biasing member is provided exerting a force on the drive sleeve towards the distal end of the medicament delivery device and a third biasing member exerting a rotational force on the last dose sleeve in a direction that causes axial displacement of the stop ring towards the distal end of the device. The provision of a second biasing member ensures reliable return of the drive sleeve towards the distal end position as the release button is moved to its inactive state. The third biasing member will enable return of the stop ring to its distal end position as soon as the plunger rod is pushed back, when a used container is replaced with a new (described in detail below).

In accordance with an embodiment of the medicament delivery device according to the invention, the first and second biasing means comprise a compression spring and the the third biasing member comprises a torsion spring. By providing a torsion spring as the third biasing means, the rotational release of the last dose sleeve is facilitated and improved.

In accordance with an embodiment of the medicament delivery device according to the invention, the first biasing means comprises a compression spring and the second and third biasing means comprise a torsion spring. Torsion springs facilitate and improve the rotational release of the last dose sleeve and the drive sleeve.

In accordance with an embodiment of the medicament delivery device according to the invention, the torsion spring of the third biasing means is located between the drive nut and the last dose sleeve.

In accordance with an embodiment of the medicament delivery device according to the invention, an outer surface of the actuator is provided with dosage indicators and wherein the locking ring has an opening therein through which opening the dosage indicators are visible. This is a simple and reliable way of presenting a set dose and allows the user to immediately realize the currently set dose.

In accordance with an embodiment of the medicament delivery device according to the invention, the locking ring is held axially immovable relative to the rear housing by means of a transparent locking ring cover. By providing a transparent locking ring cover to the rear end of the rear housing, axial immovability of the locking ring is guaranteed while still providing excellent visibility of the set dose.

In accordance with an embodiment of the medicament delivery device according to the invention, the front housing and the rear housing are interconnected and axially displaceable relative to each other by means of an outer thread on the front housing and an inner thread on the rear housing. The provision of mutually corresponding inner and outer threads ensures a reliable connection between the front and the rear housings which allows a high degree of accuracy during adjustment.

In accordance with an embodiment of the medicament delivery device according to the invention, a container holder is arranged at the front housing to receive and hold the medicament container.

In accordance with an embodiment of the medicament delivery device according to the invention, the release button comprises a snap catch element which in the active state of the release button interacts with the locking ring thereby providing the unidirectional rotational movement of the locking ring relative to the rear housing and which generates a click sound during the rotational movement. The provision of a snap catch element ensures a reliable unidirectional function and the click sound provides an audible and even a tactile feedback which is highly appreciated by many users.

In accordance with an embodiment of the medicament delivery device according to the invention, the actuator is connected to the front housing through guide means and to the rear housing through the locking ring such that the actuator is rotatably locked but axially movable in relation to said front and rear housings when said release button is in its active state. The locking ring which, when the release button is in its active position, is unidirectionally rotatable relative to the rear housing will allow the actuator to be depressed, i.e. axially moved towards its proximal position while the ring rotates on the outer threads of the actuator. The guide means allow the actuator to move axially with respect to the front housing, thus providing reliable function of the medicament delivery device of the present invention. When the release button is in the inactive position, the locking ring is bidirectionally rotatable, thus allowing the actuator to move distally under influence of the first biasing member while the ring rotates in the opposite direction on the outer threads of the actuator.

In accordance with an embodiment of the medicament delivery device according to the invention, the medicament delivery device is a pen-injector. The device according to the present invention is especially suitable when used as a pen injector.

BRIEF DESCRIPTION OF THE DRAWINGS

The invention will now be described in more detail and with reference to the appended drawings in which.

DESCRIPTION OF PREFERRED EMBODIMENTS

Figure 1:
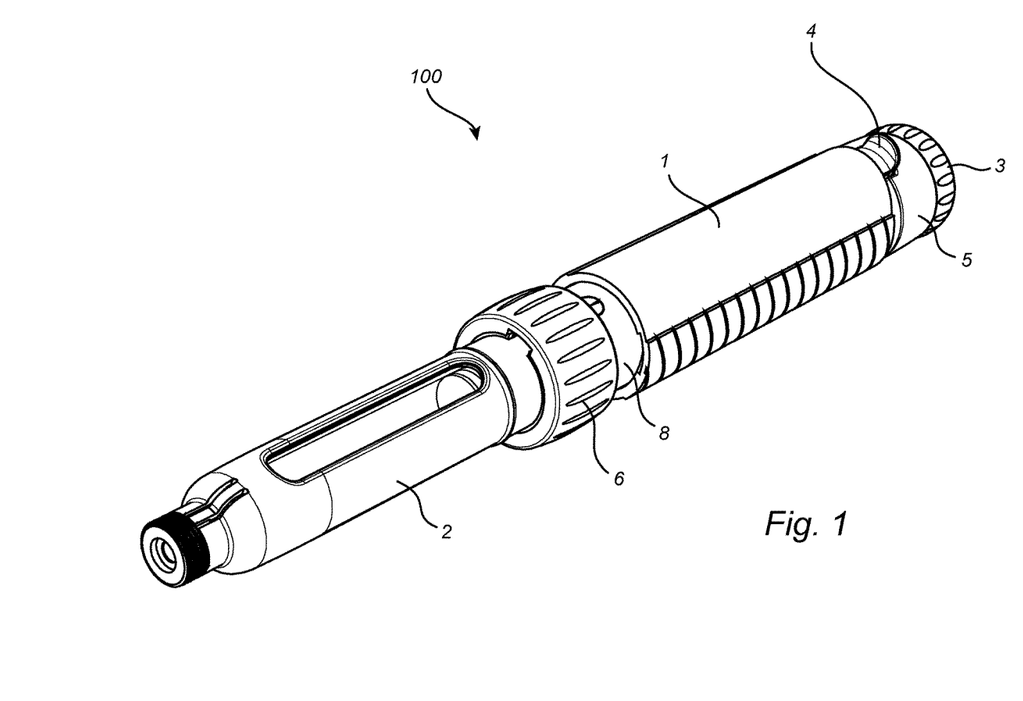
FIG. 1 is a schematic perspective view of an embodiment of the medicament delivery device according to the invention.

In a first embodiment of a medicament delivery device 100 according to the invention, as shown in FIG. 1, a medicament delivery device 100 comprises a rear housing 1 made from e.g. thermoplastic and a container holder 2. As used herein, the term "container" encompasses all types of containers suitable for injectable liquid compositions. Concerning the terms "distal" and "proximal" they refer to points which are further away and closer to the injection site respectively. At a proximal end of the medicament delivery device 100 a pen needle can be attached prior to injection. Pen needles are known in the art and can be attached to the container holder 2 by means of any known coupling means, such as a thread. The pen needle can of course also be attached to the container itself. At a distal end of the medicament delivery device 100, an actuator 3 is provided by means of which a set dose of medicament can be injected. Adjacent the actuator 3, a locking ring 5 is provided, the function of which will be described in detail below. A lock sleeve arrangement 6 having an internal and an external component is also provided, which lock sleeve arrangement interconnects the container holder 2 with a front housing 8.

Figure 2:
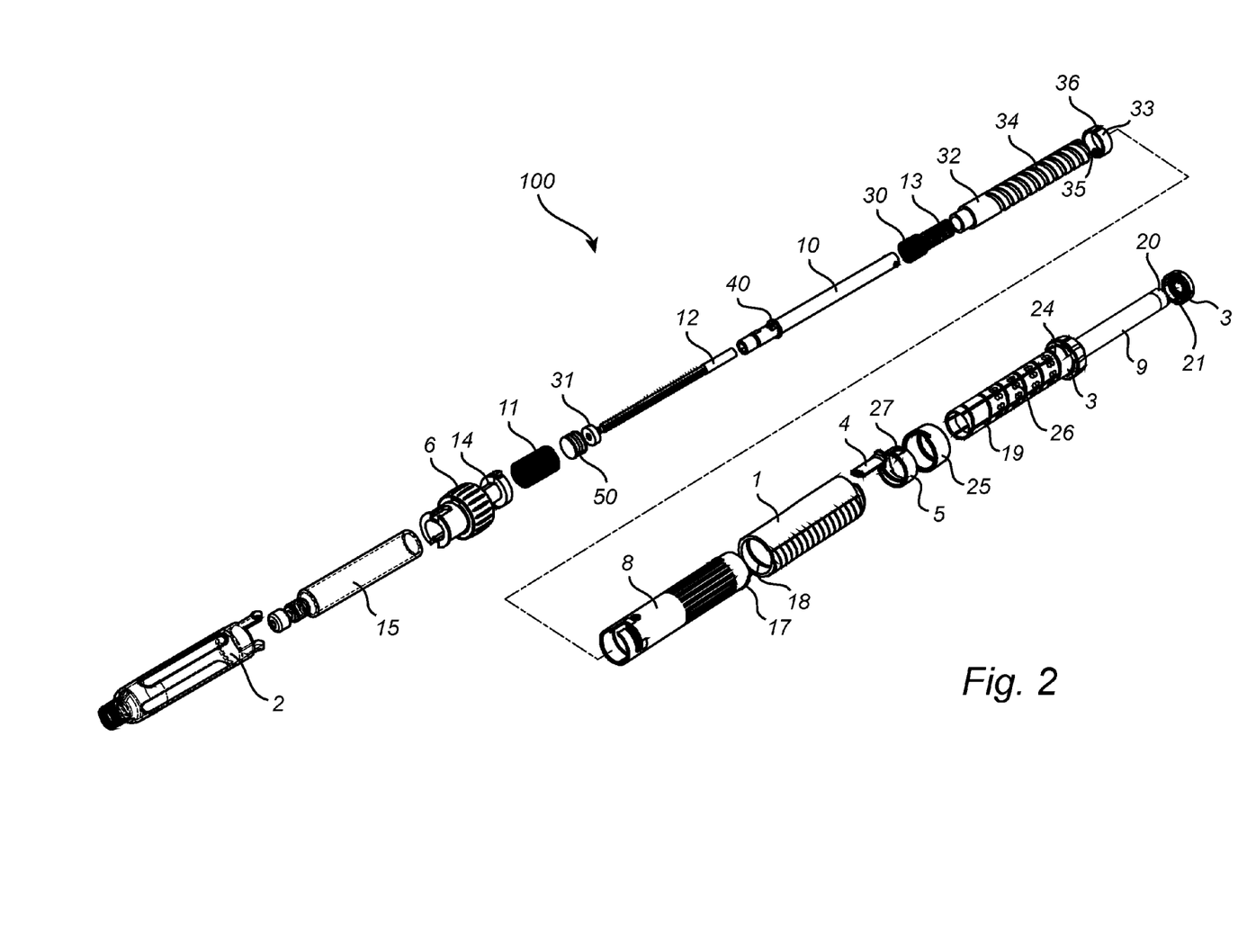
FIG. 2 is a schematic exploded perspective view of an embodiment of the medicament delivery device according to the invention.
Figure 3:
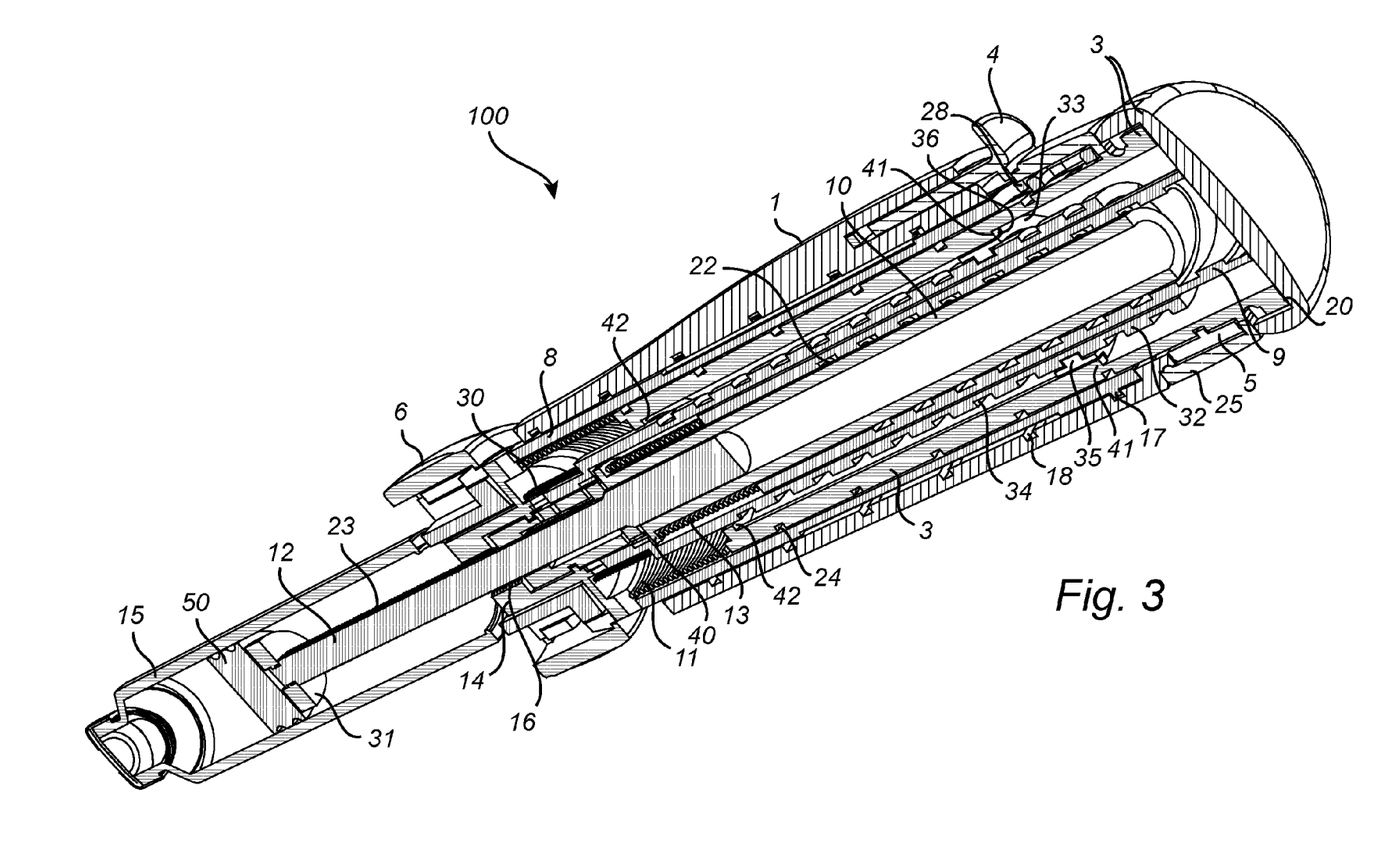
FIG. 3 is a schematic perspective cross-section of an embodiment of the medicament delivery device according to the invention.
Figure 4:
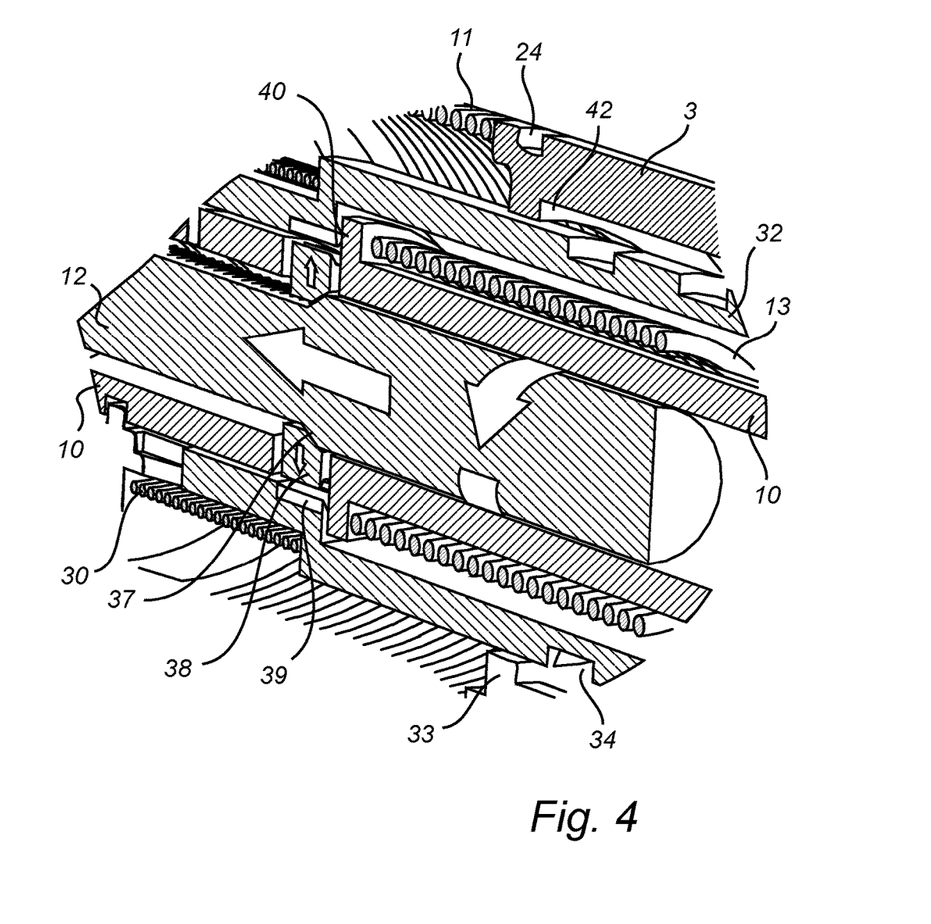
FIG. 4 is a schematic perspective cross-section of a detail of the medicament delivery device according to the invention.
Figure 5:
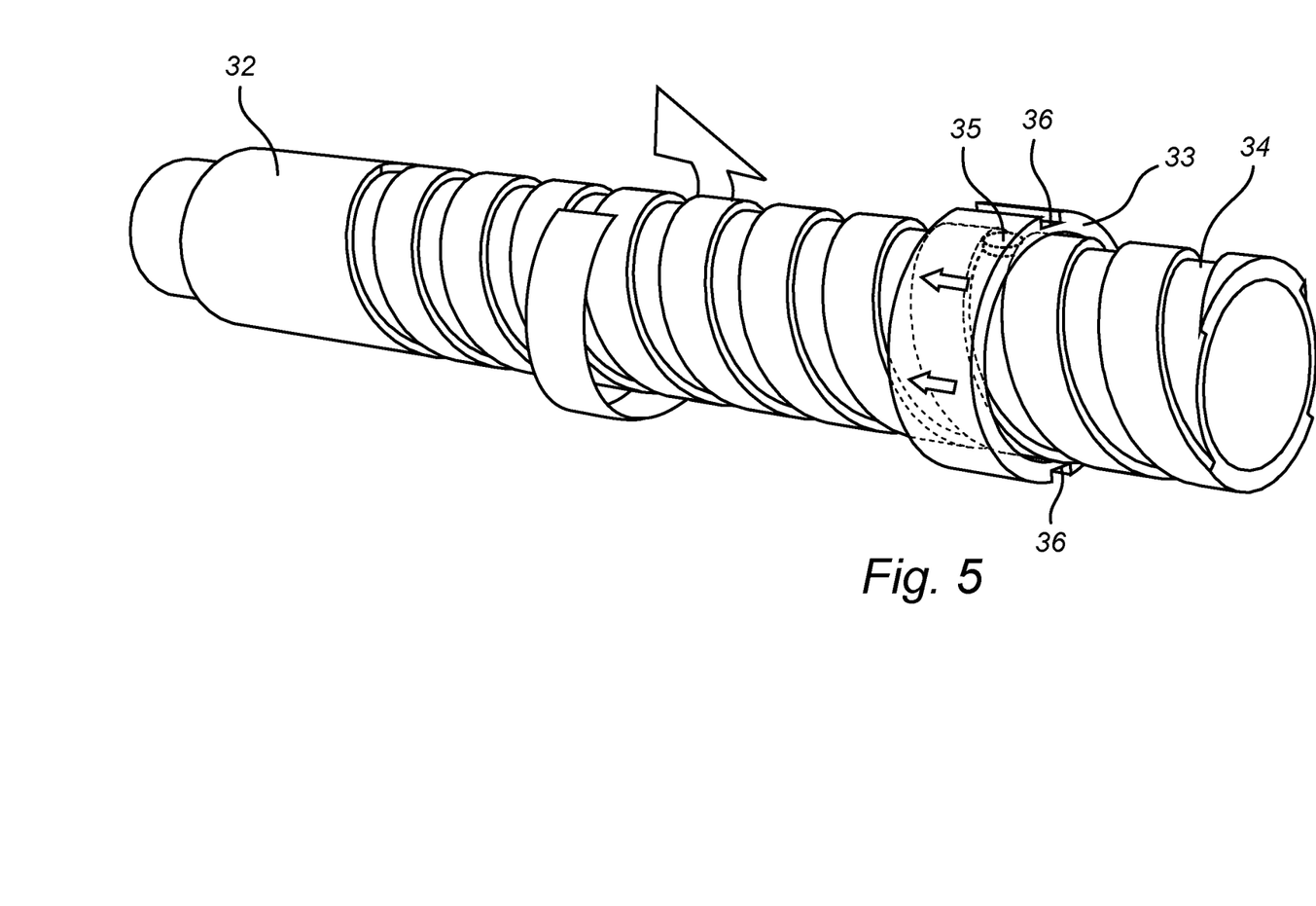
FIG. 5 is a schematic perspective view of a detail of an embodiment of the medicament delivery device according to the invention.

The build-up of a device 100 of an embodiment of the present invention will now be described, referring mainly to FIGS. 2 to 5 which show the structure of the device. FIG. 2 shows an exploded view of a first embodiment of the medicament delivery device 100 in accordance with the present invention and FIG. 3 shows a cross-sectional view which clearly describes the interaction between the different parts of the medicament delivery device 100. The device comprises a rear, outer housing 1 and a front, inner housing 8 interconnected by means of an outer thread 17 on the front housing 8 and a corresponding inner thread 18 on the rear housing 1. This threaded connection provides a dose setting arrangement for a user of the device 100. The drive nut 14, which is a split nut or two half-nuts, is fixedly arranged at a proximal end of the front housing 8 and the actuator 3 is provided within front and rear housings 1, 8. The actuator 3 is axially, i.e. linearly, movable relative to the rear, outer housing 1 and the front, inner housing 8. Corresponding guiding means 19 are provided in the form of at least one groove on the outer surface of the actuator 3 and a ridge on an inner surface of the front housing 8 (latter not shown in the figures) ensuring relative axial movability while preventing relative rotational movement of the actuator and the front housing 8. A first biasing member 11 in the form of a compression spring is arranged between the actuator 3 and the drive nut 14. The first biasing member 11 biases the actuator 3 towards a distal end position. A drive sleeve 9 is arranged axially and rotationally moveable within the actuator 3. However, in a distal end position of the drive sleeve 9 a distal end surface 20 thereof comes into contact with an inner end surface 21 of the actuator 3. The contacting end surfaces 20, 21 are provided with coupling means in the form of teeth that, when in contact with each other, will prevent relative rotational movement of the drive sleeve 9 and the actuator 3. Of course, other means than teeth can be provided in order to achieve a frictional or mechanical lock preventing relative rotational movement between the drive sleeve 9 and the actuator 3. Examples are sand paper-like surfaces; providing grooves on both surfaces; groove and ridge arrangements etc. A hollow drive rod 10 is arranged within the drive sleeve 9 and they are interconnected by means of an internal thread 22 of the drive sleeve 9 and a corresponding external thread of the hollow drive rod 10 which will convert axial movement of the drive sleeve 9 into rotational movement of the hollow drive rod 10 when the actuator 3 is depressed. The drive sleeve 9 is rotationally locked to the actuator 3 during depression due to the connecting end surfaces 20, 21, thus the drive sleeve 9 is brought along with the actuator 3 during its axial movement. A proximal end of the hollow drive rod 10 is arranged in the drive nut 14 in such a way that it can only rotate unidirectionally therein. Of course, the hollow drive rod 10 may be connected to other components, for instance to the inner surface of the front housing 8 such that the hollow drive rod 10 can only rotate unidirectionally. A second biasing member 13 in the form of a compression spring is provided between the drive sleeve 9 and an abutment collar 40 provided near a proximal end of the hollow drive rod 10 in order to force the drive sleeve 9 towards the distal end position, i.e. the position where the drive sleeve abuts the inner end surface of the actuator 3. Instead of a compression spring, a torsion spring or a combination thereof i.e. a helical spring that can be compressed and twisted can also be used. This has advantages during re-setting of the drive sleeve 9. Inside the hollow drive rod 10, in turn, a plunger rod 12 is arranged for acting on the plunger 50 of a medical container. The plunger rod 12 is arranged within the hollow drive rod 10 in such a way that relative axial movement between them is allowed while relative rotational movement is prevented. This is typically done by means of corresponding groove and ridge arrangements on the outer surface of the plunger rod 12 and the inner surface of the hollow drive rod 10 respectively. Preferably, the outer surface of the plunger rod 12 is provided with a groove and the inner surface of the hollow drive rod 10 is provided with a matching ridge extending into the groove thus preventing relative rotational movement while allowing relative axial movement. An outer surface of the plunger rod 12 is provided with threads 23 which are in threaded connection with inner threads 16 of a through bore in the drive nut 14 which is fixedly arranged at a proximal end of the front housing 8. When the actuator 3 is depressed from a distal position towards a proximal end position the end surfaces 20, 21 comes into engagement and the actuator 3 brings the drive sleeve 9 with it in the axial movement. The inner thread 22 of drive sleeve 9 interacts with the outer thread of the hollow drive rod 10 which is brought into rotational movement. The rotational movement of the hollow drive rod 10 is transferred to the plunger rod 12 and since the plunger rod 12 is in threaded connection with the drive nut 14 this rotational movement will cause the plunger rod 12 perform an axial movement as well thus forcing the plunger 50 of the medicament container forward such that a medicament is expelled from the device. The plunger rod 12 is provided with a rotatable spinner 31 at its proximal end in order to reduce friction between the rubber plunger 50 and the rotating plunger rod 12. Since the drive rod 10 is only allowed to rotate in one direction due to its connection to the drive nut 14 at its proximal end, the drive rod 10 is prevented from rotating back. In this way the plunger rod 12 does not risk being retracted (un-screwed) between doses, which could result in dose errors if the plunger rod 12 should retract from the plunger 50. The provision of this drive mechanism provides for a compact construction with excellent possibilities of achieving suitable gear ratios for user friendly pressing power vs. length of stroke and the amount of medicament to be expelled during use.

Previously known devices, such as described by WO-2004/002556 have the drawback that the actuator, when released, immediately returns to its initial position, i.e. the distal end position. This means that if the user, for some reason, releases the actuator before the complete dose has been expelled it will be hard, or even impossible to determine how large the injected amount was and how much has to be subsequently injected to arrive at the intended dose. The device 100 of the present invention therefore suggests the provision of a release button 4 and a locking ring 5 arranged on the rear housing 1. The locking ring 5 is provided with an inner thread interconnected with an outer thread 24 on an outer surface of the actuator 3. The locking ring 5 is prevented from axial movement by means of a locking ring cover 25 arranged at the rear housing 1 and is in threaded connection with an outer surface of the actuator 3 such that the locking ring is rotatable relative to the rear housing 1 but is prevented from axial movement relative to the rear housing 1 by means of the locking ring cover 25 attached to a rear part of the rear housing 1. The release button 4 is moveable between an inactive position and an active position. In the active position the release button 4 interacts with the locking ring 5 such that the locking ring can be unidirectionally rotated only, i.e. allowed to rotate in one direction and prevented from rotation in the other direction. This can be achieved by means of a snap catch element 28 which in the active state of the release button 4 interacts with teeth provided at the locking ring 5 thereby providing the unidirectional rotational movement of the locking ring 5 relative to the rear housing and generating a click sound during said rotational movement thus providing an audible and even a tactile feedback to a user. During depression of the actuator 3 the axial movement thereof will generate a rotational movement of the locking ring 5 riding on the outer thread 24 of the actuator 3. This rotational movement is allowed by the release button 4 but should the user, for some reason, let go of the actuator 3 the release button 4 and the locking ring 5 will prevent the first biasing member 11 from forcing the actuator 3 towards its distal end position. Since bi-directional rotation of the locking ring 5 is prevented and since the actuator 3 can only move axially under rotation of the locking ring 5 due to their threaded connection, the actuator 3 will remain in its current position if released. If a user, however, moves the release button 4 to its inactive state, the locking ring 5 is free to rotate in both directions and the actuator 3 and the drive sleeve 9 will assume their distal end positions forced by the respective first and second biasing members 11, 13. It should be noted that the second biasing member 13 could comprise a torsion spring instead of a compression spring or a combination thereof i.e. a helical spring that can be compressed and twisted. This is especially suitable since the drive sleeve will perform a rotational movement riding on the threads of the hollow drive rod 10 when the release button 4 is in the inactive state. The hollow drive rod 10 being unidirectionally mounted in the drive nut 14 will force the drive sleeve 9 to rotate while the hollow drive rod 14 itself remains stationary and the second biasing member 13 will facilitate this movement. When released, the actuator 3 will very quickly return to its distal end position while the drive sleeve 9, having to perform a combined axial and rotational movement, will return to the distal end position, connecting with the inner end surface 21 of the actuator 3 somewhat later i.e. with a delay. The toothed coupling between the drive sleeve 9 and the actuator 3 preferably has the same or a smaller pitch than the threaded connection between the drive sleeve 9 and the hollow drive rod 10.

Another drawback with previously known devices is that there is often no indication to the user that the contents of the container is running out and it is only discovered when the plunger rod comes to a stop before the complete dose has been injected. In order to overcome this drawback, the device of the present invention comprises a last dose sleeve 32 and a stop ring 33. The hollow last dose sleeve 32 is arranged within the actuator 3 and houses the drive sleeve 9, the hollow drive rod 10 and the plunger rod 12 in its interior. The last dose sleeve 32 is provided with a thread 34 on its outer surface and the stop ring 33 is arranged such as to encircle the last dose sleeve 32 and be in threaded connection with the thread 34 by a corresponding thread or follower 35. The stop ring 33 is provided with one or more longitudinally extending recesses 36 on its outer circumference which each interacts with a longitudinally extending ridge 41 on an inner surface of the actuator 3 such that relative axial movement of the actuator 3 and the stop ring 33 is allowed while any relative rotational movement between them is prevented. This arrangement has the result that a rotation of the last dose sleeve 32 will cause an axial movement of the stop ring 33 along the length of the last dose sleeve 32. The plunger rod 12 comprises at its distal end a funnel-like widening surface 37 and the hollow drive rod 10 comprises at its proximal end a radially displaceable clutch 38. Opposite to the radially displaceable clutch 38 of the hollow drive rod 10, the last dose sleeve 32 is provided with a corresponding clutch arrangement 39. As the plunger rod 12 advances towards a proximal end of the device 100 during use, the funnel-like widening surface 37 will come nearer the radially displaceable clutch 38 and at a predetermined point, e.g. when 80 increments, which could constitute a maximum dose to be set by the device 100, remain in the container, the funnel-like widening surface 37 will force the clutch arrangements 38, 39 into contact with each other. The clutch arrangements 38, 39 may be provided with corresponding teeth or similar such that the rotational movement of the hollow drive rod 10 will be transferred to the last dose sleeve 32. This will result in a movement of the stop ring 33 along the last dose sleeve 32 towards a proximal end of the device. The full length of travel of the stop ring 33 along the last dose sleeve 32 correspond to a maximum dose to be set, e.g. 80 increments. As long as 80 increments or more are left in the container, the maximum dose can be set by adjusting the relative axial position of the front and rear housing 8, 1 but as soon as less than 80 increments are left the stop ring 33 will travel towards the proximal end of the device. The actuator 3 is provided with an abutment surface 42 which, when the stop ring 33 has moved towards the proximal end of the device, will come into contact with the stop ring 33 thus effectively reducing the maximum dose to be set.

Figure 6:
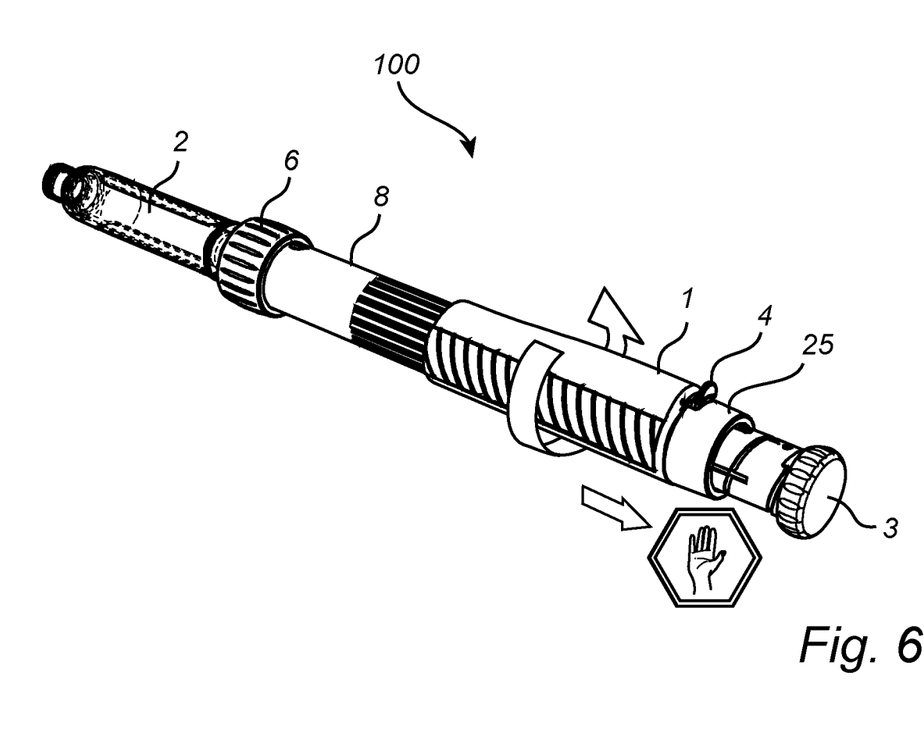
FIG. 6 is a schematic perspective view of an embodiment of the medicament delivery device according to the invention.

The function of the device 100 according to the invention will now be described. When a used, emptied container is to be replaced, the container holder 2 is twisted 90 degrees around its longitudinal axis and can thereafter be removed. This twisting also opens the drive nut 14 due to the elliptical and angled shape of the internal component of the lock sleeve arrangement 6. This function is described in the prior art document EP-0554996B1 to which reference is made. The opening of the drive nut 14 allows the user to press the plunger rod 12 towards a distal end position and push a new, full container 15 onto the plunger rod 12, typically, 3 ml containers will be used. As the plunger rod 12 is moved towards a distal end of the device, the clutch arrangements 38, 39 will eventually disconnect and as soon as this is done, a third biasing member 30, which is a torsion spring, arranged between the drive nut 14 and the last dose sleeve 32, will immediately return the stop ring 33 to its distal end position by rotation of the last dose sleeve 32. Afterwards, the container holder 2 is again locked to the device 100 by twisting it 90 degrees in the opposite direction. In a next step the release button 4 is brought to its inactive state which will cause the actuator 3 and the drive sleeve 9 to return to their distal end positions biased by the first and second biasing members 11, 13. Thereafter, a required dose is set by adjusting the relative axial position of the rear housing 1 and the front housing 8 by screwing them in or out until a preferred dose has been set. As long as more than 80 increments remain in the container, the distal end position of the actuator 3 is defined by the guiding means in the front housing 8 and the proximal end position of the actuator 3 is defined by the rear housing 1 since the relative axial position of the front housing 8 with regard to the rear housing 1 determines the length of stroke of the actuator 3, which in turn corresponds to a set dose. The pitch of the threaded connection between the rear housing 1 and the front housing 8 corresponds to that between the actuator 3 and the locking ring 5 and the actuator 3 is rotatably locked relative to the front housing 8. Therefore, the locking ring 5 will follow any rotational movement of the rear housing 1. The actuator 3 is provided with dose indications 26 on the outer surface thereof. These dose indications are visible through a dose window 27 in the locking ring 5 and since the locking ring cover 25 is transparent, this window is visible at all time. Unlike some prior art devices, where a dose set too high cannot be made undone, a user of a device 100 according to present invention can adjust the dose upwards and downwards until a required dose has been set. This makes the device 100 according to the present invention more user friendly and cost-effective. This since a dose set too high in a prior art device had to be discarded and a new, correct dose be set before injection could be preformed. A flexing bump in the front housing 8 snaps on the inner surface of the rear housing 1, thus giving a tactile indication to the user for each dose increment. This also prevents the rear housing 1 from rotating on the front housing 8 during injection. As soon as the user has set a required dose, which can readily be seen in the dose window, a needle is attached and the medicament can be injected. If the injection is halted at any point the locking ring 5 and the actuator 3 will stop at that position, with the remaining part of the dose showing in the dose window. The user therefore has complete control of the injection process all the time. When a user is ready to inject the next dose, the release button 4 is brought to its inactive position and the actuator 3 will return to its distal end position. If the user intends to inject the same dose as the last time, no dose has to be set since the last dose is still set by the relative position of the rear housing 1 and front housing 8. As soon as less than the maximum dose to be set remain in the container 15 the stop ring 33 will start travelling towards the proximal end of the device when the actuator 3 is depressed. If a user tries to set a dose which is higher than what is left in the container 15 the setting will come to a stop as indicated in FIG. 6. The user sees the remaining maximum amount to be injected in the dose window 27 and now has two possibilities. Either inject the remaining amount in a first step and thereafter reload the device 100 with a new container and inject a remainder in a subsequent injection. Or, if this is too inconvenient, discard the old container 15 and reload the device 100 with a new container 15 and inject the full dose in a single step.

Finally, it is realized, that a medicament delivery device according to the invention has a number of advantages over the known prior art devices. Due to the fact that the device has a completely mechanical design, reliability can be ensured at all time without being dependent on batteries or similar. The actuator 3 will not automatically return to its distal end position when released. The set dose will not have to be reset for each injection occasion, instead the device according to the present invention provides an automatic dose memory. If the remaining amount of medicament in the container falls below the required dose, the user will be informed of this and also the remaining amount of medicament in the container prior to injection and can therefore decide if the injection should be done in one or two steps. It is re-usable and the user can change the emptied container to a new container in a simple manner. The device allows for a variable dose size and the setting of the dose can be set downwardly and upwardly during the dose setting until a required dose has been set. The set dose is shown in the dose window 27 and during injection the remaining dose to be injected is always shown in a countdown manner. The fact that the remaining amount of the dose to be delivered is always shown in the dose window 27 gives the device according to the present invention another great advantage over prior art devices. If there is not enough medicament in the container, the user just reads the dose indication 26 in the dose 27 window and thereafter a new container is loaded and the remaining dose can be set and injected, thus arriving at the required total dose.

It is to be understood that the embodiments described above and in the drawings are to be regarded only as non-limiting examples of the invention and that they may be modified in many ways within the scope of the claims.

The invention claimed is:

1. A medicament delivery device having a proximal end and a distal end, the medicament delivery device comprising:
   a front housing and a rear housing interconnected and axially displaceable relative to each other between an extended position and a retracted position;
   a plunger rod movable between a proximal end position and a distal end position and configured to act on a plunger of a medicament container;
   a drive mechanism configured to drive the plunger rod;
   an actuator connected to the front and rear housings and axially movable in the front and rear housings between a proximal end position and a distal end position, wherein the actuator is biased by a first biasing member toward the distal end position;
   a drive sleeve releasably connected to the actuator and configured to act on the drive mechanism to drive the plunger rod;
   a locking ring rotatably disposed at a distal end of the rear housing and in threaded connection with an outer surface of the actuator, wherein the locking ring is prevented from axial movement relative to the rear housing;
   a release button arranged on the rear housing and movable between an active state and an inactive state, wherein the release button in the active state allows unidirectional rotational movement of the locking ring relative to the rear housing such that the actuator is movable axially toward the proximal end position under rotational movement of the locking ring, the release button in the inactive state allows bidirectional rotational movement of the locking ring relative to the rear housing such that the actuator is movable axially toward the proximal end position or toward the distal end position under rotational movement of the locking ring, and the proximal end position of the actuator is defined by the axial position of the rear housing such that adjusting the mutual axial position of the front housing with relative to the rear housing determines a stroke length between the distal end position of the actuator and the proximal end position of the actuator thereby enabling setting a medicament dose; and
   a last dose limiting mechanism configured to interact with the drive mechanism and limit the distal end position of the actuator when the plunger rod has reached a predetermined position between its distal end position and its proximal end position.

2. The medicament delivery device of claim 1, wherein the drive mechanism comprises:
   a drive nut fixedly arranged near a proximal end of the front housing, the drive nut comprising a through bore, and a part of the bore having an inner thread;
   a hollow drive rod having an outer thread, wherein the hollow drive rod is unidirectionally rotatably mounted with a proximal end thereof in the drive nut;
   wherein the plunger rod is arranged within the hollow drive rod and in threaded connection with the inner thread of the bore, the plunger rod and the hollow drive rod are configured to mate with each other such that axial movement of the plunger rod relative to the hollow drive rod is allowed and rotation of the plunger rod relative to the hollow drive rod is prevented, and the drive sleeve is arranged in threaded connection with the outer thread of the hollow drive rod.

3. The medicament delivery device of claim 2, wherein the last dose limiting mechanism comprises:
   a last dose sleeve rotatable within the actuator, the last dose sleeve enclosing at least partly the hollow drive rod and including an external thread; and
   a stop ring in threaded connection with the external thread of the last dose sleeve and configured to mate with the actuator and prevent rotation of the stop ring relative to the actuator such that rotational movement of the last dose sleeve results in axial movement of the stop ring from a distal end position toward a proximal end position along a length of the last dose sleeve;
   wherein the actuator comprises an abutment surface configured to interact with the stop ring.

4. The medicament delivery device of claim 3, wherein the plunger rod includes a funnel-like widening surface near its distal end, and the hollow drive rod includes a radially displaceable clutch configured to contact the last dose sleeve by the funnel-like widening surface of the plunger rod such that rotation of the hollow drive rod, and thus the plunger rod, causes the last dose sleeve to rotate thereby axially displacing the stop ring toward a proximal end of the device and re-locating the distal end position of the actuator toward the proximal end of the device, thereby preventing setting a medicament dose that exceeds an amount of medicament remaining in the medicament container.

5. The medicament delivery device of claim 2, wherein the drive sleeve is within and axially movable relative to the actuator, and the device further comprises a coupler configured to prevent the drive sleeve and actuator from rotational movement relative to each other when the drive sleeve is in a distal axial end position relative to the actuator.

6. The medicament delivery device of claim 5, wherein the coupler comprises a tooth coupling provided on an inside surface of a distal end of the actuator.

7. The medicament delivery device of claim 6, wherein a pitch of the tooth coupling is the same or less than a pitch of the threaded connection between the drive sleeve and the hollow drive rod.

8. The medicament delivery device of claim 3, further comprising a second biasing member that exerts a force on the drive sleeve toward the distal end of the medicament delivery device and a third biasing member that exerts a rotational force on the last dose sleeve in a direction that causes axial displacement of the stop ring toward the distal end of the device.

9. The medicament delivery device of claim 8, wherein the first and second biasing members each comprise a compression spring, and the third biasing member comprises a torsion spring.

10. The medicament delivery device of claim 9, wherein the torsion spring of the third biasing member is located between the drive nut and the last dose sleeve.

11. The medicament delivery device of claim 8, wherein the first biasing member comprises a compression spring, and the second and third biasing members each comprise a torsion spring.

12. The medicament delivery device of claim 11, wherein the torsion spring of the third biasing member is located between the drive nut and the last dose sleeve.

13. The medicament delivery device of claim 1, wherein an outer surface of the actuator includes dosage indicators, and the locking ring has an opening therein through which the dosage indicators are visible.

14. The medicament delivery device of claim 1, wherein the locking ring is held axially immovable relative to the rear housing by a transparent locking ring cover.

15. The medicament delivery device of claim 1, wherein the front housing and the rear housing are interconnected and axially displaceable relative to each other through an outer thread on the front housing and an inner thread on the rear housing.

16. The medicament delivery device of claim 1, further comprising a container holder arranged at the front housing to receive and hold the medicament container.

17. The medicament delivery device of claim 1, wherein the release button comprises a snap catch element that interacts with the locking ring providing unidirectional rotational movement of the locking ring relative to the rear housing in the active state of the release button and that generates a click sound during the rotational movement.

18. The medicament delivery device of claim 1, wherein the actuator is connected to the front housing through a guide and to the rear housing through the locking ring such that the actuator is rotatably locked but axially movable in relation to the front and rear housings when the release button is in its active state.

19. The medicament delivery device of claim 1, wherein the medicament delivery device is a pen-injector.

* * * * *